(12) United States Patent
Eger et al.

(10) Patent No.: US 7,201,927 B2
(45) Date of Patent: Apr. 10, 2007

(54) NUTRITIONAL OLIVE OIL BASED COMPOSITIONS, AND METHOD OF CONSUMPTION THEREOF

(75) Inventors: Shaul Eger, Yokneam Moshava (IL); Ishak Ne'eman, Haifa (IL)

(73) Assignee: Dr. Eger-Olive Oil Products Industry Ltd., Yokneam Moshava (IL)

( * ) Notice: Subject to any disclaimer, the term of this patent is extended or adjusted under 35 U.S.C. 154(b) by 0 days.

(21) Appl. No.: 11/261,640

(22) Filed: Oct. 31, 2005

(65) Prior Publication Data

US 2006/0093688 A1    May 4, 2006

(51) Int. Cl.
*A61K 36/00*   (2006.01)
(52) U.S. Cl. ...................................... 424/725
(58) Field of Classification Search ...................... None
See application file for complete search history.

(56) References Cited

U.S. PATENT DOCUMENTS 6,117,476 A * 9/2000 Eger et al. .................. 426/601
6,156,369 A * 12/2000 Eger et al. .................. 426/601

FOREIGN PATENT DOCUMENTS

IL    WO0150873    *   7/2001

OTHER PUBLICATIONS en.wikipedia.org/wiki/Hydroxy_acid.*
umm.edu/altmed/ConsSupplements/AlphaLipoicAcids.*
en.wikipedia.org/wiki/Omega-3_fatty_acids.*

* cited by examiner

*Primary Examiner*—Christopher R. Tate
*Assistant Examiner*—Melenie McCormick
(74) *Attorney, Agent, or Firm*—Mark M. Friedman

(57) ABSTRACT

A nutritional, olive-oil based, at least semi-solid product for oral intake and for topical application, the product including: (a) an olive oil; (b) an omega-3 fatty acid source, and (c) an emulsifier, the components being intimately mixed so as to form the at least semi-solid product, and wherein a Total Water Content (TWC) within the product is within a range of 0.25% to 3%, by weight.

23 Claims, No Drawings

NUTRITIONAL OLIVE OIL BASED COMPOSITIONS, AND METHOD OF CONSUMPTION THEREOF

This application draws priority from U.S. Provisional Patent Application Ser. No. 60/466,409, filed Apr. 30, 2003, and from PCT Patent Application Ser. No. IL04/000350, filed Apr. 25, 2004.

FIELD AND BACKGROUND OF THE INVENTION

The present invention relates generally to natural, edible-oil based compositions, and more particularly, to compositions based on olive oil and an omega-3 fatty acid source as active ingredients.

Food spreads such as margarine and butter are high-volume food products. In recent years, attention has been directed to producing healthier food spreads, in the form of reduced fat alternatives to the existing products.

Margarines contain a water phase and an oil phase, which are emulsified, generally in the form of a water-in-oil emulsion. The taste of margarines and food spreads is due mostly to water soluble flavors, oil soluble flavors and salt included in the water phase. Conventional margarines contain at least 80% fat by weight. The fat content is made up mainly of polysaturated fats. In the production of margarine, the polysaturated fats are hydrogenated. These hydrogenated products are readily acidified to produce free radical carcinogenic compounds.

Many attempts have been made to formulate low fat spread products, in order to reduce the caloric content of the spread and other dietetic considerations, and in some cases, to reduce the cost of raw materials.

Various non-triglyceride substances have been described as potential fat-replacers in food products. Examples of such non-triglyceride substances are waxes, e.g. jojoba oil and hydrogenated jojoba oil, polysiloxanes, acylated glycerides, polyalkoxyglycerolethers, dicarboxylic acid esters, polyol fatty acid polyesters and the epoxy-extended derivatives thereof. Examples of disclosures of fat-replacers are U.S. Pat. Nos. 3,600,186, 4,005,195 and 4,005,196.

A substance that has widely been applied as a fat-extender is water. This use of water has, for example, led to the introduction of so-called halvarines. If relatively high levels of water are used, often thickening agents and/or gelling agents are used for avoiding adverse effects of the high water level. Such margarine substitutes typically contain up to 60% water.

In particular, effort has been directed towards the development of fat-replacement compositions that provide the smooth mouthfeel and oily taste of conventional spreads, and do not provide a bad after-taste or cause malodor.

Another approach to new, oil-based food spread products is the use of various natural edible oils. The therapeutic properties of oils from natural origins, such as olive oil and avocado oil, have been widely documented. Olive oil has been indicated as having a therapeutic effect in stomach ailments, improving memory, decreasing mortality from heart disease due to increasing blood flow, and softening skin. Additionally, olive oil is used in relieving ear infection, may reduce the risk of certain cancers, decreases calcium loss from bones, and increases mineral absorption. In children, olive oil has been linked to stimulating growth and development.

The properties of olive oil result from its chemical structure. Olive oil is made up of 75% oleic acid, monounsaturated fatty acid, approximately 14% polyunsaturated fatty acids, mainly linoleic acid and about 11% saturated fatty acids. Oleic acid, the main constituent of olive oil is very stable and is therefore less readily acidified to produce carcinogenic free radicals. In contrast, conventional margarine consists of mainly (64%) polysaturated fatty acids and only 30% monounsaturated fatty acids.

Some natural oils, such as olive oil, are known for alleviating skin problems of different kinds. The human skin may be afflicted by various conditions and ailments, some of which are cosmetic in nature (e.g., blemishes, dryness, reddishness, pimples, spots, discolorations, scars, nicks, diaper rash, sunburn, wrinkles), and some of which are medical ailments (e.g., severe acne, burns, cuts, scrapes, chafes, warts, venous insufficiency, ulcers).

Various salves, creams and unguents exist to relieve some or all of these conditions. These often contain synthetic oils and fats, minerals and preservatives. In addition, many conditions exist for which the available preparations are of dubious efficacy.

It would therefore be highly advantageous to have olive-oil based compositions characterized by improved nutritional characteristics, superior texture and flow properties, and greatly improved shelf-life with respect to the known oil-based and natural-oil based compositions.

SUMMARY OF THE INVENTION

According to the teachings of the present invention there is provided a nutritional, olive-oil based, at least semi-solid product for oral intake and for topical application, the product including: (a) an olive oil; (b) an omega-3 fatty acid source, and (c) an emulsifier, the olive oil, the omega-3 fatty acid source, and the emulsifier being intimately mixed so as to form the at least semi-solid product, and wherein a Total Water Content (TWC) within the product is within a range of 0.25% to 3%, by weight.

According to further features in the described preferred embodiments, the product contains 40% to 92.5%, by weight, of the olive oil, more preferably, 55% to 85%, and most preferably, 60% to 80%.

According to still further features in the described preferred embodiments, the product contains 0.5% to 20%, by weight, of the omega-3 fatty acid source.

According to still further features in the described preferred embodiments, the TWC within the product is at least 0.3% and below 2%.

According to still further features in the described preferred embodiments, the product contains 5% to 12%, by weight, of the emulsifier, and more preferably, 7 to 10% by weight.

According to still further features in the described preferred embodiments, the emulsifier includes at least one emulsifier selected from the group consisting of a monoglyceride and a palmitic fatty acid.

According to still further features in the described preferred embodiments, the product further includes ascorbyl palmitate.

According to still further features in the described preferred embodiments, the Total Oxygen Content (TOC) within the product is below 1% by volume.

According to still further features in the described preferred embodiments, a container containing the product contains a Total Oxygen Content (TOC) of less than about 3% by volume.

According to still further features in the described preferred embodiments, the weight ratio of the olive oil to the omega-3 fatty acid source is between 2:1 and 30:1, and preferably, between 4:1 and 10:1.

According to still further features in the described preferred embodiments, the weight ratio of the olive oil to the emulsifier is between 4:1 and 15:1.

According to still further features in the described preferred embodiments, the product further includes vitamin C.

According to still further features in the described preferred embodiments, the product further includes alpha lipoic acid.

According to still further features in the described preferred embodiments, the product contains 0.03% to 0.3%, by weight, of the vitamin C.

According to still further features in the described preferred embodiments, the product further includes both vitamin C and alpha lipoic acid.

According to still further features in the described preferred embodiments, the product further includes both vitamin C and an alpha hydroxy acid.

According to still further features in the described preferred embodiments, the product contains 0.5% to 10%, by weight, of the alpha hydroxy acid.

According to another aspect of the present invention there is provided a method of using a nutritional, olive-oil based, at least semi-solid product, the method including the steps of: (a) providing the olive-oil based product, the product including an olive oil, an omega-3 fatty acid source, and an emulsifier, and wherein a total water content (TWC) within the product is at least 0.25% and below 3%, the olive oil, the omega-3 fatty acid source, and the emulsifier being intimately mixed so as to form the at least semi-solid product, and (b) effecting consumption of the olive-oil based product by a user, the consumption selected from the group consisting of ingestion of the product and topical application of the product on a skin surface.

According to further features in the described preferred embodiments, the consumption of the product is effected by ingestion of the product.

According to further features in the described preferred embodiments, the consumption of the product is effected by the topical application of the product, wherein the product is effective in at least partially ameliorating at least one symptom of a dermatological condition when topically applied.

According to yet another aspect of the present invention there is provided a composition including two or more oils from natural sources so that the final composition monounsaturated fatty acids and omega-3 fatty acids. The amount of monounsaturated fatty acids includes at least 40% (preferably 50%, more preferably 60%) by weight. Although any amount of omega-3 fatty acids may have a desired effect, the inventor currently believes that a noticeable effect begins when there is at least 0.2% by weight omega-3 fatty acids, preferably more than 1%, and even more preferably more than 5%. Even higher amounts of omega-3 fatty acids such as greater than 10% or even 20% have been shown to be exceptionally effective.

In a preferred embodiment, the composition of the present invention includes antioxidants, preferably natural antioxidants.

In an additionally preferred embodiment, the composition of the present invention also includes one or more additives including ascorbyl palmitate, alpha and or beta hydroxy acids, other glycolic acids, alpha lipoic acids, tocotrienol and dimethyl amino ethanol (DMAE).

A most preferred substance for use as an omega-3 fatty acid component of the composition of the present invention is fish oil.

A most preferred substance for use as a monounsaturated fatty acid component of the composition of the present invention is olive oil, which also naturally contains antioxidants such as vitamin E and polyphenols.

A preferred formulation of the composition of the present invention includes about 70% by weight olive oil and about 20% by weight fish oil.

The term "carriers" as used in this specification and the accompanying claims includes, but is not limited to, vegetable oils such as sunflower oil or soybean oil.

According to still further features in the described preferred embodiments the emulsifier includes at least one item selected from the group consisting of a monoglyceride and a palmitic fatty acid. Alternately, or additionally, PO5 may be employed for emulsification.

According to still further features in the described preferred embodiments the alpha hydroxy acid includes a lactic acid, for example lactic acid derived from sugar cane.

According to still further features in the described preferred embodiments the alpha hydroxy acid is 0.5 to 10% of the composition by weight, more preferably 1 to 5%, most preferably about 2.5%.

According to still further features in the described preferred embodiments the pharmaceutical composition further includes dimethylamino ethanol (DMAE) When DMAE is included, it may be advantageous to add small quantities (i.e. PPM concentrations) of essential oils to mask the unpleasant smell.

According to still further features in the described preferred embodiments the emulsifier is selected from the group consisting of a monoglyceride and a palmitic fatty acid.

DETAILED DESCRIPTION OF THE INVENTION

The present invention is of nutritional based compositions based on olive oil and an omega-3 fatty acid source as active ingredients, and a method of consumption thereof.

The present invention can be used as a topical pharmaceutical composition to provide at least symptomatic relief from a variety of dermatological conditions. The present invention can be used to relieve venous insufficiency, relieve symptoms of viral infection, promote wound healing and prevent skin graft rejection.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

According to one aspect of the present invention there is provided a pharmaceutical composition. The pharmaceutical composition includes as an active ingredient a mixture of an olive oil and an omega-3 fatty acid source with an emulsifier. Carriers and excipients are included as required. The pharmaceutical composition is effective in at least partially ameliorating at least one symptom of a dermatological condition when topically applied. This type of pharmaceutical composition finds especial utility in treatment of venous insufficiency, for example in treatment of diabetic ulcers.

According to some preferred formulations, 40% to 92.5% of the pharmaceutical composition by weight is olive oil, more preferably 60 to 80%, most preferably about 70%.

According to some preferred formulations of the pharmaceutical composition the at least one omega-3 fatty acid is 0.5% to 20% by weight of the composition. According to various preferred embodiments, the omega-3 fatty acid source may include, for example, a fish oil, a primrose oil, a flaxseed oil, a safflower oil, or a bourage oil.

According to still another aspect of the present invention there is provided an additional pharmaceutical composition. The additional pharmaceutical composition includes as an active ingredient a physiologically active mixture of an olive oil and a vitamin-derived antioxidant and an alpha hydroxy acid with an emulsifier, carriers and excipients as required. The additional pharmaceutical composition is effective in at least partially ameliorating at least one symptom of a dermatological condition when topically applied. This type of pharmaceutical composition finds especial utility in treatment of herpes virus symptoms, burns, skin graft acceptance, cuts (e.g. resulting from shaving) abrasions, scars (e.g. blood vessels, acne scars).

Optionally, but preferably, the pharmaceutical composition further includes dimetlhylaminio ethanol (DMAE). When DMAE is included, it may be advantageous to add small quantities (i.e. PPM concentrations) of essential oils to mask the unpleasant smell.

Most generally the composition is made up of a combination of natural oils from plant or animal sources (preferably not mineral or synthetic) so that the composition includes cis-monounsaturated fatty acids, omega 3 fatty acids and antioxidants. Preferred oils used in making a composition of the present invention include but are not limited to olive oil, avocado oil, peanut oil, canola oil, camelina oil, walnut oil, nut oils, macadamia oil, flaxseed oil, linseed oil, perilla oil, fish oil, sesame oil, wheat germ oil, jojoba oil, evening primrose oil, borage oil, palm oil and vernonia oil.

It is preferred that the oils used in preparing the composition of the present invention do not include fatty acids that are distilled, hardened, hydrogenated or are of the trans form. It is important to note that exceptions can be found. In naturally occurring non-processed palm oil there are saturated fats. At the same time palm oil has a high percentage of anti-oxidants. Thus, palm oil is a good anti-oxidant source according to the present invention.

Most preferred is a combination of olive oil as a source of monounsaturated fatty acids and fish oil as a source of omega 3 fatty acids.

It has been found that the efficacy of the composition of the present invention is unexpectedly increased by the addition of one or more of the following additives: ascorbyl palmitate, alpha and or beta hydroxy acids, other glycolic acids, alpha lipoic acids, tocotrienol and dimethyl amino ethanol (DMAE).

One skilled in the art recognizes that the teachings of U.S. Pat. No. 6,117,476, U.S. Pat. No. 6,156,369 and/or PCT Publication No. WO 03/005831, all of which are incorporated by reference as if fully set forth herein, provide methods for preparing the compositions of the present invention in a semi-solid form (spreads, ointments, etc.). These teachings require only moderate heating, such that the molecular structures or chemical compositions of the present invention are not substantially affected.

Although many of the oils used in the present invention naturally include antioxidants (e.g., olive oil contains 150 mg/l vitamin E and 350 mg/l polyphenols), it has been found that the supplemental addition of antioxidants in relatively high concentrations amplifies the healing effects of the composition of the present invention far beyond what would be expected by one skilled in the art. There is an apparent synergistic effect of the monounsaturated fatty acid, the omega-3 fatty acid and the antioxidant.

Preferred antioxidants are: ascorbyl palmitate, alpha and or beta hydroxy acids, other glycolic acids, alpha lipoic acids and tocotrienol.

Another preferred additive is dimethyl amino ethanol (DMAE) known for use in rejuvenating the skin and treating wrinkles in the skin.

An exceptionally effective composition and thus a currently preferred embodiment of the present invention is made by combining 70 g olive oil, 20 g fish oil, 7 g monoglyceride and 2 g PO5 in accordance with the teachings of U.S. Pat. No. 6,117,476, U.S. Pat. No. 6,156,369 and/or PCT publication WO 03/005831. To this basic composition it has been found useful to add one or more of the following: up to 1 g ascorbyl palmitate and/or 1 g lipoic acid and/or 1 g DMAE and/or up to 5 g alpha hydroxy acid (such as glycolic acid, lactic acid).

The above-referenced patents do not teach, nor fairly suggest, that topical application of olive-oil based formulations of the disclosed compositions is desirable or advantageous.

Moreover, it has surprisingly been discovered that in compositions containing more than about 3% water, the water content deleteriously affects the stability of the semi-solid product, such that the nutritional value and product shelf-life are seriously compromised. Since the compositions of the present invention are markedly more effective without the presence of preservatives, the limiting of the water content within narrow bounds is a significant aspect of the invention.

As used herein in the specification and in the claims section that follows, the term "total water content" (TWC) refers to the total amount of water present in the product, in all forms: as free water, as dissolved water, etc. Specifically, the term TWC is meant to include the water present in natural oils such as olive oil.

Preferably, the olive-oil based products of the present invention should contain a TWC of less than 3%, more preferably, less than 2.5%, still more preferably, less than 2%, and most preferably, less than 1.5%. It has also been found that the TWC should be at least 0.1%, more preferably, at least 0.2%, and most preferably, at least 0.25%.

One method of ensuring that the olive-oil based products of the present invention contain a suitably-low TWC includes pre-drying of the olive oil, which naturally contains up to 0.6% water.

The inventors have further discovered that the compositions of the present invention are extremely sensitive to the presence of oxygen, which deleteriously affects the stability of the semi-solid product, such that the nutritional value and product shelf-life are seriously compromised. One source of oxygen is oxygen dissolved in the product. A more prevalent source of oxygen is residual or occluded oxygen. Without wishing to be limited by theory, the inventors believe that the fatty acids in the composition of the present invention, being mono-unsaturated and poly-unsaturated, are particularly susceptible to oxidation.

As used herein in the specification and in the claims section that follows, the terms "residual oxygen" and "occluded oxygen" refer to oxygen gas, disposed in the at least semi-solid product (e.g., spread, paste, ointment) of the present invention and/or to a pocket of gas containing oxygen disposed between the product and a inside wall of a container (e.g., tube) containing the product.

As used herein in the specification and in the claims section that follows, the term "total oxygen content" (TOC) with respect to the at least semi-solid product (e.g., spread, paste, ointment) of the present invention, refers to the total amount of oxygen, in volume %, disposed in the at least semi-solid product. The total amount of oxygen includes the sum of the residual oxygen and the relatively minute quantities of dissolved oxygen.

As used herein in the specification and in the claims section that follows, the term "total oxygen content" (TOC) with respect to a container containing the at least semi-solid product (e.g., spread, paste, ointment) of the present invention, refers to the total amount of oxygen, in volume %, disposed in the container, and equals the sum of the TOC with respect to the at least semi-solid product and the volume % of oxygen disposed between the product and a inside wall of a container (e.g., tube) containing the product.

The TOC in a container containing the at least semi-solid product should be less than 3%, preferably less than 2%, more preferably less than 1%, and most preferably, less than 0.5%. In order to achieve such low TOCs, and given the relatively high viscosities of the products of the present invention, a combination of several preparation techniques may be advantageously employed, including: preparation in a nitrogen (or other inert) environment, filling of tubes with the product under pressure, and subsequent subjection of the tubes to sub-atmospheric pressure.

As used herein in the specification and in the claims section that follows, the term "fully natural", with respect to the product of the present invention, refers to a product that is free of artificial preservatives.

Use of compositions according to the present invention includes the topical application of the composition of the present invention to treat a dermatological condition. Generally once or twice daily use of an amount of composition that covers the affected area in its entirety has proven to be effective.

The composition of the present invention has been applied to treat various skin ailments of various humans. Equal efficacy is expected for non-human animals, especially mammals.

In various formulations the composition of the present invention has been found to be efficient in mitigating the discomfort of dry skin, irritated skin, chaffed skin, wounded skin, ulceric skin, sunburned skin or otherwise UV-damaged skin.

It has also been found that the composition of the present invention has a mitigating and healing effect on ulcers typical of patients afflicted with diabetes.

The composition of the present invention has been found efficient in the prevention of scars, for example, when applied to wounds after surgery.

The composition of the present invention has also been found effective in accelerating the healing of wounds.

Preliminary experiments on a variety of lesions, wounds, chaffs, scrapes, scars and other skin ailments such as dermatitis, seborrhea, eczema, third-degree burns, diabetic ulcers, psoriasis have all shown a clear and definite sanative and palliative effect.

In general compositions of the present invention have shown analgesic, anti-inflammatory, moisturizing, antipruritic, astringent, emollient, sanative and antiedemic effects.

EXAMPLE

Relief of Venous Insufficiency

Reference is now made to the following example, which together with the above descriptions, illustrate the invention in a non-limiting fashion.

Materials and Methods

Olive Oil/Omega-3: An olive oil base containing 20% fish oil which includes 30% EPA+DHA plus a palm oil derived monoglyceride. The olive oil base has been treated such that the TWC of the preparation is 0.35%. The preparation is manufactured under pasteurizing conditions and vacuum pressure (−0.1 Atmosphere).

Aqua-cream: Emulsifying wax, wood alcohol, white soft paraffin, liquid paraffin, water (47%) and vitamin E.

Fourteen patients with persistent bilateral venous insufficiency of the feet and legs were employed in the study. Patients topically applied aqua-cream to one leg/foot and Olive Oil/Omega-3 according to the present invention to the opposing leg/foot.

Olive Oil/Omega-3 according to the present invention was far superior to the control Aqua-cream with 4/14 (29%) of patients reporting significant reduction in symptoms and 8/14 (57%) reporting disappearance of dry skin/cracks in the Olive Oil/Omega-3 treated leg. In sharp contrast, only 4/14 patients (29%) reported improvement in the Aqua-cream treated leg.

These results indicate the compositions of the present invention are superior to a conventional cream of the prior art. The results were presented at the 30th Annual Conference of the Israeli Society of Plastic Surgery, November 2003.

The present invention is not limited to the embodiments described herein but encompasses any and all embodiments a within the scope of the claims, including obvious variants thereof. Such obvious variants include diluting the composition of the present invention with unsuitable oils and fatty acids.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed:

1. A food spread product comprising:
   (a) a container, and
   (b) a nutritional, olive-oil based, at least semi-solid food spread, disposed within said container, said food spread including:

(i) an olive oil;
(ii) an omega-3 fatty acid source;
(iii) an emulsifier,
said olive oil, said omega-3 fat acid source, and said emulsifier being intimately mixed so as to form said at least semi-solid food spread,
wherein a Total Water Content within the food spread is less than about 3%, by weight,
wherein a Total Oxygen Content within said container is below 3%, by volume, and wherein said food spread is substantially free of any artificial preservative.

2. The food spread product of claim 1, wherein said food spread contains 40% to 92.5%, by weight, of said olive oil.

3. The food spread product of claim 1, wherein said food spread contains 0.5% to 20%, by weight, of said omega-3 fatty acid source.

4. The food spread product of claim 1, wherein said Total Oxygen Content within said container is below 2%, by volume.

5. The food spread product of claim 1, wherein said Total Oxygen Content within said container is below 1%, by volume.

6. The food spread product of claim 1, wherein said Total Oxygen Content within said container is below 0.5%, by volume.

7. The food spread product of claim 2, wherein said Total Oxygen Content within said container is below 1%, by volume.

8. The food spread product of claim 2, said food spread further including alpha lipoic acid.

9. The food spread product of claim 2, wherein said Total Water Content within said composition is less than about 1%, by weight.

10. An olive-oil based skin product, comprising:
(a) a container, and
(b) a nutritional, olive-oil based, at least semi-solid composition, disposed within said container, for topical application on a skin surface, said composition including:
(i) an olive oil;
(ii) an omega-3 fatty acid source;
(iii) an emulsifier,
said olive oil, said omega-3 fatty acid source, and said emulsifier being intimately mixed so as to form said at least semi-solid composition,
wherein a Total Water Content within said composition is less than about 3%, by weight,
wherein a Total Oxygen Content within said container is below 3%, by volume, and wherein said at least semi-solid composition is substantially free of any artificial preservative.

11. The skin product of claim 10, the product being effective in at least partially ameliorating at least one symptom of a dermatological condition when topically applied.

12. The skin product of claim 11, wherein said Total Oxygen Content within said container is below 1%, by volume.

13. The skin product of claim 10, wherein said Total Oxygen Content within said container is below 0.5%, by volume.

14. The skin product of claim 10, wherein said at least semi-solid composition contains 40% to 92.5%, by weight, of said olive oil.

15. The skin product of claim 11, further including alpha lipoic acid.

16. A method comprising the steps of:
(a) providing a food spread product comprising:
(i) a container, and
(ii) a nutritional, olive-oil based, at least semi-solid food spread, disposed within said container, said food spread including:
(A) an olive oil;
(B) an omega-3 fatty acid source;
(C) an emulsifier,
said olive oil, said omega-3 fatty acid source, and said emulsifier being intimately mixed so as to form said at least semi-solid food spread,
wherein a Total Water Content within said food spread is less than about 3%, by weight,
wherein a Total Oxygen Content within said container is below 3%, by volume, and wherein said spread is substantially free of any artificial preservative, and
(b) ingesting said nutritional, olive-oil based, at least semi-solid food spread.

17. The method of claim 16, wherein said Total Oxygen Content within said container is below 1%, by volume.

18. The method of claim 16, further comprising the step of:
(c) effecting a deoxygenation treatment, prior to step (a), so as to produce said Total Oxygen Content within said food spread product.

19. A method comprising the steps of:
(a) providing a skin product comprising:
(i) a container, and
(ii) a nutritional, olive-oil based, at least semi-solid composition, disposed within said container, said composition including:
(A) an olive oil;
(B) an omega-3 fatty acid source;
(C) an emulsifier,
said olive oil, said omega-3 fatty acid source, and said emulsifier being intimately mixed so as to form said composition,
wherein a Total Water Content within said composition is less than about 3%, by weight,
wherein a Total Oxygen Content within said container is below 3%, by volume, and wherein said composition is substantially free of any artificial preservative, and
(b) topically applying said composition on a skin surface of a user.

20. The method of claim 19, wherein said skin product is effective in at least partially ameliorating at least one symptom of a dermatological condition when topically applied.

21. The method of claim 20, wherein said Total Oxygen Content within said container is below 1%, by volume.

22. The method of claim 19, wherein said Total Oxygen Content within said container is below 0.5%, by volume.

23. The method of claim 19, further comprising the step of:
(c) effecting a deoxygenation treatment, prior to step (a), so as to produce said Total Oxygen Content within said skin product.

* * * * *